US012807904B2

(12) United States Patent
Wieland et al.

(10) Patent No.: US 12,807,904 B2
(45) **Date of Patent: *Nov. 24, 2026**

(54) STORAGE-STABLE LIQUID DETERGENT OR CLEANING AGENT CONTAINING PROTEASE AND CELLULASE

(71) Applicant: BASF SE, Ludwigshafen (DE)

(72) Inventors: Susanne Wieland, Zons/Dormagen (DE); Karl-Heinz Maurer, Erkrath (DE); Timothy O'Connell, Duesseldorf (DE); Hendrik Hellmuth, Duesseldorf (DE)

(73) Assignee: BASF SE, Ludwigshafen (DE)

( * ) Notice: Subject to any disclaimer, the term of this patent is extended or adjusted under 35 U.S.C. 154(b) by 801 days.

This patent is subject to a terminal disclaimer.

(21) Appl. No.: 18/178,328

(22) Filed: Mar. 3, 2023

(65) Prior Publication Data

US 2023/0399589 A1 Dec. 14, 2023

Related U.S. Application Data

(63) Continuation of application No. 15/804,507, filed on Nov. 6, 2017, now abandoned, which is a continuation of application No. 13/993,923, filed as application No. PCT/EP2011/072509 on Dec. 13, 2011, now abandoned.

(30) Foreign Application Priority Data

Dec. 17, 2010 (DE) ......................... 102010063457.2

(51) Int. Cl.

| | |
|---|---|
| ***C11D 3/386*** | (2006.01) |
| ***C12N 9/42*** | (2006.01) |
| ***C12N 9/54*** | (2006.01) |

(52) U.S. Cl.

CPC ...... *C11D 3/38663* (2013.01); *C11D 3/38618* (2013.01); *C11D 3/38645* (2013.01); *C12N 9/2437* (2013.01); *C12N 9/54* (2013.01)

(58) Field of Classification Search

CPC ................ C07D 401/06; C07D 417/14; C07D 417/06; C07D 401/14; A61K 45/06; A61K 31/4439; A61P 25/00

See application file for complete search history.

(56) References Cited

U.S. PATENT DOCUMENTS

| | | | | |
|---|---|---|---|---|
| 5,877,141 | A * | 3/1999 | Gabriel | C11D 3/38663 510/393 |
| 6,599,730 | B1 | 7/2003 | Brode, III et al. | |
| 9,163,226 | B2 * | 10/2015 | Wieland | C11D 7/36 |
| 12,415,973 | B2 * | 9/2025 | Degering | C11D 1/83 |
| 2012/0238005 | A1 * | 9/2012 | Wieland | C11D 3/361 510/393 |
| 2013/0280794 | A1 | 10/2013 | Wieland et al. | |
| 2018/0155659 | A1 | 6/2018 | Wieland et al. | |

FOREIGN PATENT DOCUMENTS

| | | | |
|---|---|---|---|
| CA | 2325159 | A1 | 5/2001 |
| EP | 1240525 | A2 | 9/2002 |
| EP | 1305432 | A2 | 5/2003 |
| EP | 1921147 | A2 | 5/2008 |
| EP | 2074205 | A1 | 7/2009 |
| WO | WO-92/06165 | A1 | 4/1992 |
| WO | WO-1992/21760 | A1 | 12/1992 |
| WO | WO-95/10615 | A1 | 4/1995 |
| WO | WO-95/23221 | A1 | 8/1995 |
| WO | WO-96/29397 | A1 | 9/1996 |
| WO | WO-97/14804 | A1 | 4/1997 |
| WO | WO-98/12307 | A1 | 3/1998 |
| WO | WO-02/099091 | A2 | 12/2002 |
| WO | WO-2009/015951 | A1 | 2/2009 |
| WO | WO-2009/030632 | A1 | 3/2009 |
| WO | WO-2011/032988 | A1 | 3/2011 |
| WO | WO-2014/030097 | A2 | 2/2014 |
| WO | WO-2014/030097 | A3 | 4/2014 |

OTHER PUBLICATIONS

Yadav et al. Assessing the compatibility of choline-based deep eutectic solvents for the structural stability and activity of cellulase: Enzyme sustain at high temperature. International Journal of Biological Macromolecules (2023), 249, 125988 (Year: 2023).*

Altschul, S., et al., "Basic Local Alignment Search Tool," *Journal of Molecular Biology*, 1990, vol. 215, pp. 403-410.

Altschul, S., et al., "Gapped BLAST and PST-BLAST: a New Generation of Protein Database Search Programs," *Nucleic Acids Research*, 1977, vol. 25, No. 17, pp. 3389-3402.

Bender, M., et al., "The Determination of the Concentration of Hydrolytic Enzyme Solutions: «- Chymotrypsin, Trypsin, Papain, Elastase, Subtilisin, and Acetylcholinesterase," *Journal of the American Chemical Society*, 1966, vol. 88, No. 24, pp. 5890-5913.

Chenna, R., et al., "Multiple Sequence Alignment With the Clustal Series of Programs," *Nucleic Acids Research*, 2003, vol. 31, No. 13, pp. 3497-3500.

Del Mar, C., et al., "A Sensitive New Substrate for Chymotrypsin," *Analytical Biochemistry*, 1979, vol. 99, pp. 316-320.

European patent application No. 17179938.0, Extended European Search Report, 8 pp. dated Oct. 9, 2017.

Gornall, A., "Determination of Serum Proteins by Means of the Biuret Reaction," *Journal of Biological Chemistry*, 1949, vol. 177, No. 2, 751-766.

Guo et al., Protein tolerance to random amino acid change, Proc. Natl. Acad. Sci. USA, 101(25):9205-10 (2004).

(Continued)

*Primary Examiner* — Iqbal H Chowdhury

(74) *Attorney, Agent, or Firm* — MARSHALL, GERSTEIN & BORUN LLP

(57) ABSTRACT

According to the invention, storage stability in terms of cellulolytic activity is to be improved in a liquid washing or cleaning agent which comprises a protease and cellulase. This is achieved by the use of a protease which comprises an amino acid sequence which is at least 80% identical to the amino acid sequence specified in SEQ ID NO. 1 and which has the amino acid glutamic acid (E) or aspartic acid (D) or the amino acid asparagine (N) or glutamine (Q) or the amino acid alanine (A) or glycine (G) or serine (S) at position 99 in the count according to SEQ ID NO. 1.

1 Claim, No Drawings

Specification includes a Sequence Listing.

(56) References Cited

OTHER PUBLICATIONS

Heringa, J. et al., "Increasing thermal stability of subtilisin from mutations suggested by strongly interacting side-chain clusters," *Protein Engineering*, 1995, vol. 8, No. 1 pp. 21-30.
International Search Report in international application No. PCT/EP2011/072509, dated Oct. 29, 2012.
Lever, M., "A New Reaction for Colorimetric Determination of Carbohydrates," *Analytical Biochemistry*, 1972, No. 47, pp. 273-279.
Lever, M., "Carbohydrate Determination with 4-Hydroxybenzoic Acid Hydrazide (PAHBAH): Effect of Bismuth on the Reaction," *Analytical Biochemistry*, 1977, vol. 81, pp. 21-27.
Notredame, C., "T-Coffee: A Novel Method for Fast and Accurate Multiple Sequence Alignment," *Journal of Molecular Biology*, 2000, vol. 302, 205-217.
Van Raay, H, et al., "Zur Bestimmung der Proteolytischen Aktivität in Enzymkonzentraken und Enzymhaltigen Wasch-, Spül-, und Reinigungsmitteln," *Tenside Detergents* (1970), 7.3, pp. 125-132.
Zaccolo et al., The effect of high-frequency random mutagenesis on in vitro protein evolution: a study on TEM-1 beta-lactamase, J. Mol. Biol., 285(2):775-83 (1999).
Nielsen, L., et al., "Design of Liquid Enzyme Products with Built-In Liquid Detergent Stabilization System," Chemical Product Design: Toward a Perspective through Case Studies, pp. 149-163 (2007).

* cited by examiner

SEQUENCE LISTING

```
Sequence total quantity: 8
SEQ ID NO: 1            moltype = AA  length = 269
FEATURE                 Location/Qualifiers
source                  1..269
                        mol_type = protein
                        organism = Bacillus lentus
SEQUENCE: 1
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGRG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 2            moltype = AA  length = 269
FEATURE                 Location/Qualifiers
source                  1..269
                        mol_type = protein
                        organism = Bacillus lentus
SEQUENCE: 2
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGEG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 3            moltype = AA  length = 269
FEATURE                 Location/Qualifiers
source                  1..269
                        mol_type = protein
                        organism = Bacillus lentus
SEQUENCE: 3
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGDG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 4            moltype = AA  length = 269
FEATURE                 Location/Qualifiers
source                  1..269
                        mol_type = protein
                        organism = Bacillus lentus
SEQUENCE: 4
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGNG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 5            moltype = AA  length = 269
FEATURE                 Location/Qualifiers
source                  1..269
                        mol_type = protein
                        organism = Bacillus lentus
SEQUENCE: 5
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGQG AISSIAQGLE WAGNNGMHVA  120
NLSLGSPSPS ATLEQAVNSA TSRGVLVVAA SGNSGASSIS YPARYANAMA VGATDQNNNR  180
```

-continued

```
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 6            moltype = AA  length = 269
FEATURE                 Location/Qualifiers
source                  1..269
                        mol_type = protein
                        organism = Bacillus lentus
SEQUENCE: 6
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGAG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 7            moltype = AA  length = 269
FEATURE                 Location/Qualifiers
source                  1..269
                        mol_type = protein
                        organism = Bacillus lentus
SEQUENCE: 7
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGGG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269

SEQ ID NO: 8            moltype = AA  length = 269
FEATURE                 Location/Qualifiers
source                  1..269
                        mol_type = protein
                        organism = Bacillus lentus
SEQUENCE: 8
AQSVPWGISR VQAPAAHNRG LTGSGVKVAV LDTGISTHPD LNIRGGASFV PGEPSTQDGN  60
GHGTHVAGTI AALNNSIGVL GVAPSAELYA VKVLGADGSG AISSIAQGLE WAGNNGMHVA  120
NLSLGSPSPS ATLEQAVNSA TSRGVLVVAA SGNSGASSIS YPARYANAMA VGATDQNNNR  180
ASFSQYGAGL DIVAPGVNVQ STYPGSTYAS LNGTSMATPH VAGAAALVKQ KNPSWSNVQI  240
RNHLKNTATS LGSTNLYGSG LVNAEAATR                                    269
```

STORAGE-STABLE LIQUID DETERGENT OR CLEANING AGENT CONTAINING PROTEASE AND CELLULASE

CROSS-REFERENCE TO RELATED APPLICATIONS

This application is a continuation of U.S. patent application Ser. No. 15/804,507, filed Nov. 6, 2017, which is a continuation of U.S. patent application Ser. No. 13/993,923, which is the U.S. National Stage application of International Application No. PCT/EP2011/072509, filed Dec. 13, 2011, which claims priority under 35 U.S.C. § 119 to German Patent Application No. 102010063457.3, filed Dec. 17, 2010; the entire contents of these applications are hereby incorporated by reference in their entirety.

INCORPORATION BY REFERENCE OF MATERIAL SUBMITTED ELECTRONICALLY

The Sequence Listing, which is a part of the present disclosure, is submitted concurrently with the specification in XML format. The name of the file containing the Sequence Listing is "47662132_Seqlisting.XML" which was created on Mar. 3, 2023, and is 9,613 bytes in size. The sequence listing contained in this file is part of the specification and is hereby incorporated by reference herein in its entirety.

The invention lies in the field of the liquid washing and cleaning agents. The invention relates in particular to liquid, enzyme-containing washing and cleaning agents that comprise defined proteases in combination with a cellulase, and in addition proposes methods, in which such agents are used. The invention further relates to uses of defined proteases in liquid washing or cleaning agents that comprise a cellulase.

Proteases of the subtilisin type are preferably employed in washing and cleaning agents. The proteases incorporated in washing or cleaning agents known in the prior art either stem originally from microorganisms, such as the genera *Bacillus, Streptomyces, Humicola*, or *Pseudomonas*, and/or are produced according to known biotechnological processes using suitable microorganisms, for example by transgenic expression hosts of the genera *Bacillus* or by filamentary fungi.

Modern liquid washing agents in particular increasingly comprise additional enzymes, among which are especially cellulases (endoglucanases). A cellulase is an enzyme that catalyses the hydrolysis of 1,4-β-D-glucosidic bonds in cellulose (cellobiose), and/or lichenin and/or β-D-glucans. They are often also capable of hydrolysing the 1,4-bonds in β-D-glucans that in addition to 1,4-bonds also possess 1,3-bonds. Within the EC classification of enzymes, in the digital classification system for enzymes, cellulases have the EC number ("Enzyme Commission Number") 3.2.1.4 and consequently belong to the third of the six main classes of enzyme, the hydrolases (E.C.3.-.-.-), hereunder to the glycosylases (E.C. 3.2.-.-) and again hereunder to the glycosidases (E.C. 3.2.1.-), i.e. enzymes that hydrolyse O- and/or S-glycosyl compounds. Cellulases are capable of decomposing cellulose to β-glucose. Consequently, cellulases act in particular on cellulose-containing or cellulose derivative-containing residues in the wash and catalyse their hydrolysis.

In the international patent application WO 95/23221 there are disclosed proteases or protease variants of the subtilisin type from *Bacillus lentus* DSM 5483 which are suitable for use in washing or cleaning agents. Among these proteases is also one that can possess an amino acid exchange R99E, A, S or G. It is also disclosed that the washing agents can comprise additional enzymes, among them also a cellulase. The washing agents can be solid or liquid. However, this document does not directly and clearly disclose a liquid washing agent that comprises a cellulase in combination with a protease that possesses the amino acid glutamic acid (E) or aspartic acid (D) or the amino acid asparagine (N) or glutamine (Q) or the amino acid alanine (A) or glycine (G) or serine (S) at the location 99. The same is true for the European patent application EP 1 921 147.

A disadvantage of protease-containing and cellulase-containing liquid washing and cleaning agents from the prior art is that they are not sufficiently storage stable and consequently, even after a short time, lose a considerable amount of cellulolytic and/or proteolytic, especially cellulolytic activity. The presence of protease frequently leads to the loss of cellulolytic activity as the protease inactivates the cellulase. The washing or cleaning agent then does not exhibit an optimal cleaning power.

The present invention is based on the object of overcoming the cited disadvantage and to the provision of protease-containing and cellulase-containing liquid washing or cleaning agents that are adequately or better storage stable, in particular in regard to their cellulolytic activity.

A subject matter of the invention is therefore a liquid washing or cleaning agent, containing (a1) a protease that contains an amino acid sequence that is at least 80% identical to the amino acid sequence listed in SEQ ID NO: 1 and that has the amino acid glutamic acid (E) or aspartic acid (D) at location 99 in the count according to SEQ ID NO: 1, or (a2) a protease that contains an amino acid sequence that is at least 80% identical to the amino acid sequence listed in SEQ ID NO: 1 and that has the amino acid asparagine (N) or glutamine (Q) at location 99 in the count according to SEQ ID NO: 1, or (a3) a protease that contains an amino acid sequence that is at least 80% identical to the amino acid sequence listed in SEQ ID NO: 1 and that has the amino acid alanine (A) or glycine (G) or serine (S) at location 99 in the count according to SEQ ID NO: 1, and (b) a cellulase.

It was surprisingly found that a liquid washing or cleaning agent that comprises a combination of such a protease with a cellulase is advantageously storage stable. In particular it exhibits a higher cellulolytic activity after storage compared with a washing or cleaning agent that differs from an inventive agent solely by the protease that is present in the respective agent, wherein at the beginning of storage the protease is present in the same concentration in the agents under comparison, relative to active enzyme. A protease provided in the context of the present invention therefore leads to a reduced inactivation of the cellulase. The reduced inactivation of cellulase by the protease provided in the context of the present invention is not, however, the result of an inadequate protease activity.

In this regard an agent according to the invention possesses and preferably still has a good, especially advantageous, cleaning power on protease-sensitive soils. A cleaning power of this type in regard to at least one protease-sensitive soil also occurs in particular at low temperatures, for example between 10° C. and 50° C., preferably between 10° C. and 40° C. or between 20° C. and 40° C. Such an agent therefore enables an adequate or improved removal of at least one, preferably a plurality of protease-sensitive soils on fabrics and/or hard surfaces, for example dishes.

In regard to the international patent application WO 95/23221 mentioned in the introduction, the present invention thus concerns a particularly advantageous choice that affords a highly productive and storage stable liquid washing agent, particularly in regard to the proteolytic and/or cellulolytic activity of the agent or residual activity of the agent after storage.

In the context of the invention, cleaning power is understood to mean the lightening power on one or more soils, especially washing soils. Examples of such stains are blood-milk/ink on cotton, whole egg/pigment on cotton, chocolate-milk/ink on cotton, peanut oil-pigment/ink on polyester/cotton, grass on cotton or cocoa on cotton, especially of the type listed below. In the context of the invention, not only the washing or cleaning agent that contains the protease and the cellulase or the wash or cleaning liquor formed by this agent, but also the protease or the cellulase itself, has a particular cleaning power. Therefore the cleaning power of the enzymes contributes to the cleaning power of the agent and the wash or cleaning liquor formed by the agent. The cleaning power is preferably determined as presented below.

"Washing or cleaning liquor" is understood to mean that solution comprising the washing or cleaning agent which acts on textiles or fabrics (washing liquor) or on hard surfaces (cleaning liquor), and thereby comes into contact with the stains that are present on the textiles and/or fabrics or hard surfaces. The washing or cleaning liquor usually comes into being when the washing or cleaning process begins and the washing or cleaning agent is dissolved or diluted with water, for example in a washing machine or in another suitable container.

In the context of the invention, storage stability exists if a washing or cleaning agent according to the invention exhibits a higher cellulase activity after storage compared to a control composition that differs from the washing or cleaning agent according to the invention only in the protease comprised in the control composition. Consequently, after storage a washing or cleaning agent according to the invention exhibits a higher residual activity of the cellulase compared to the control. Thus, at the beginning of storage both of the agents to be compared exhibit the same amount or concentration of cellulase and/or initial cellulolytic activity. Furthermore, at the beginning of storage both of the agents possess the same concentration of protease, based on active enzyme, and both agents are treated in the same manner, in particular in regard to the storage conditions and the determination of the enzyme activity. Storage takes place with increasing preference for at least 24 hours, 48 hours, 72 hours, 5 days, 1 week, 2 weeks, 3 weeks, 4 weeks or 8 weeks. Moreover, storage preferably takes place at a temperature of 20° C., 25° C. or 30° C., particularly preferably at 30° C.

In this regard, the enzyme activity can be determined using standard methods matched to the particular enzyme type. Methods for determining the enzyme activities are well known to the person skilled in the field of enzyme technology and are routinely used by him. Methods for measuring the protease activity, for example, are disclosed in Tenside, vol. 7 (1970), pp. 125-132. The proteolytic activity can also be determined from the release of the chromophore para-nitroaniline (pNA) from the substrate suc-L-Ala-L-Ala-L-Pro-L-Phe-p-nitroanilide (suc-AAPF-pNA). The protease cleaves the substrate and releases pNA. The released pNA causes the extinction at 410 nm to increase; the change in extinction as a function of time is a measure of the enzymatic activity (see Del Mar et al., 1979). The measurement is carried out at a temperature of 25° C., at pH 6 and a wavelength of 410 nm. The measurement period is 5 minutes with a measurement interval of 20 s to 60 s. The protease activity is preferably given in PU (protease units).

The cellulose activity is measured using a standard method. The cellulase activity is preferably determined as follows. Cellulases release glucose from CMC (carboxymethyl cellulose). Samples are incubated under defined reaction conditions (100 mM sodium phosphate buffer pH 7.5, 40° C., 15 min) with a substrate (1.25% CMC). The reaction with p-hydroxybenzoic acid hydrazide (PAHBAH) in the presence of bismuth affords a yellow dye that can be determined photometrically at 410 nm. A condition is an alkaline pH during the color reaction. The quantity of released sugar corresponding to the coloration is a measure of the enzyme activity (see Lever, Anal. Biochem., 1972, 47 & 1977, 81).

In the context of the present invention, the existence of enzyme stabilization is particularly preferably determined as listed above by using a protease-containing and cellulase containing liquid washing or cleaning agent that has been stored for at least four and at most 8 weeks at a temperature of 30° C., wherein the proteolytic activity is determined from the release of the para-nitroaniline chromophore (pNA) from the substrate suc-AAPF-pNA, and the cellulolytic activity is determined as described above.

The protease comprised in a washing or cleaning agent according to the invention contains an amino acid sequence that is at least 80% identical to the amino acid sequence listed in SEQ ID NO: 1 and has the amino acid glutamic acid (E) or aspartic acid (D) or the amino acid asparagine (N) or glutamine (Q) or the amino acid alanine (A) or glycine (G) or serine (S) at location 99 in the count according to SEQ ID NO: 1. The identity of the amino acid sequence matches the amino acid sequence listed in the SEQ ID NO: 1, increasingly preferably to at least 81%, 82%, 83%, 84%, 85%, 86%, 87%, 88%, 89%, 90%, 91%, 92%, 93%, 94%, 95%, 96%, 97%, 98%, 99% and quite particularly preferably to 100%. SEQ ID NO: 1 is the sequence of the mature alkaline protease from *Bacillus lentus* DSM 5483 which is disclosed in the international patent application WO 92/21760, the disclosure of which being hereby expressly referred to.

It has been inventively demonstrated that by adding such a protease to a liquid washing or cleaning agent that comprises a cellulase, a particularly storage stable liquid washing agent is obtained, especially in regard to its residual cellulolytic activity after storage, especially after a period of storage with increasing preference for at least 24 hours, 48 hours, 72 hours, 5 days, 1 week, 2 weeks, 3 weeks, 4 weeks or 8 weeks.

A protease comprised in a washing or cleaning agent according to the invention exhibits a proteolytic activity, i.e. it is capable of hydrolysing peptide bonds of a polypeptide or protein. It is therefore an enzyme that catalyzes the hydrolysis of peptide bonds and is thus capable of cleaving peptides or proteins. In particular it is a subtilase and particularly preferably a subtilisin.

A cellulase is an enzyme as described in the introduction. Synonymous expressions can be used for cellulases, in particular endoglucanase, endo-1,4-beta-glucanase, carboxymethylcellulase, endo-1,4-beta-D-glucanase, beta-1,4-glucanase, beta-1,4-endoglucanhydrolase, celludextrinase or avicelase. The determining factor of whether an enzyme is a cellulase in the context of the invention, is its ability to hydrolyse 1,4-β-D-glucosidic bonds in cellulose.

Inventively conditionable cellulases (endoglucanases, EG) include for example the fungal, endoglucanase (EG)-rich cellulase preparation or its further developments that are offered by the Novozymes Company under the trade name Celluzyme®. The products Endolase® and Carezyme® based on the 50 kD-EG, respectively 43 kD-EG from Humicola insolens DSM 1800 are also obtainable from the Novozymes Company. Further useable commercial products from this company are Cellusoft®, Renozyme® and Celluclean®. Cellulases, for example, which are available under the trade names Ecostone® and Biotouch® from AB Enzymes, Finland can also be used and which are at least partially based on the 20 kD-EG from *Melanocarpus*. Additional cellulases from the AB Enzymes Company are Econase® and Ecopulp®. Further suitable cellulases are from *Bacillus* sp. CBS 670.93 and CBS 669.93, the CBS 670.93 from *Bacillus* sp. being available under the trade name Puradax® from the Danisco/Genencor Company. Additional useable commercial products of the Danisco/Genencor Company are “Genencor detergent cellulase L” and IndiAge® Neutra.

Variants of these enzymes obtained by point mutations can also be inventively incorporated. Particularly preferred cellulases are Thielavia terrestris cellulase variants, which are disclosed in the international application WO 98/12307, cellulases from *Melanocarpus*, in particular *Melanocarpus albomyces*, which are disclosed in the international application WO 97/14804, cellulases of the EGIII type from *Trichoderma reesei*, which are disclosed in the European patent application EP 1 305 432 or variants that can be obtained from them, in particular those that are disclosed in the European patent applications EP 1 240 525 and EP 1 305 432, as well as cellulases, which are disclosed in the international patent applications WO 1992006165, WO 96/29397 and WO 02/099091. Reference is therefore expressly made to their respective disclosure or their disclosed content in this regard is therefore expressly incorporated into the present patent application.

In another embodiment of the invention, the washing or cleaning agent is wherein the protease further comprises at least one of the following amino acids in the count according to SEQ ID NO: 1:

(a) threonine at position 3 (3T),
(b) isoleucine at position 4 (4I),
(c) alanine, threonine or arginine at position 61 (61A, 61T or 61R),
(d) aspartic acid or glutamic acid at position 154 (154D or 154E),
(e) proline at position 188 (188P),
(f) methionine at position 193 (193M),
(g) isoleucine at position 199 (199I),
(h) aspartic acid, glutamic acid or glycine at position 211 (211D, 211E or 211G),
(i) combinations of the amino acids (a) to (h).

Thus the protease, in addition to the cited amino acids at position 99, has one or more of the abovementioned amino acids at the respective positions. These amino acids can bring about further advantageous properties and/or even reinforce properties that are already present. In particular the abovementioned amino acids bring about an increase in the proteolytic activity and/or in the stability of the protease in a liquid washing or cleaning agent or in the wash liquor formed by this washing or cleaning agent. By adding such a protease to a liquid washing or cleaning agent that comprises a cellulase, a particularly storage stable liquid washing or cleaning agent is likewise obtained, especially in regard to its residual cellulolytic activity after storage, but preferably also in regard to its residual proteolytic activity after storage, especially after a period of storage with increasing preference for at least 24 hours, 48 hours, 72 hours, 5 days, 1 week, 2 weeks, 3 weeks, 4 weeks or 8 weeks. Such an agent also shows improved cleaning powers on protease-sensitive and/or cellulase-sensitive soils.

The amino acid positions are hereby defined by an alignment of the amino acid sequence of the protease to be added with the amino acid sequence of the protease from *Bacillus lentus*, as is listed in SEQ ID NO: 1. As the protease from *Bacillus* lentus represents an important reference molecule in the prior art to describe proteases and amino acid modifications, it is advantageous to refer to the count of the protease from *Bacillus lentus* (SEQ ID NO: 1) in the assignment of the amino acid positions. Furthermore, the count conforms to the mature protein. This classification should also be used if the amino acid sequence of the protease to be added contains a greater number of amino acid residues than the protease from *Bacillus lentus* according to SEQ ID NO: 1.

Starting from the cited positions in the amino acid sequence of the protease from *Bacillus lentus*, the amino acid positions in a protease to be inventively added are those that are attributed to these same positions in an alignment.

In addition to position 99, particularly advantageous positions are consequently the positions 3, 4, 61, 154, 188, 193, 199 and 211, attributed in an alignment with SEQ ID NO: 1 and thus in the count according to SEQ ID NO: 1. The following amino acid residues in the wild type molecule of the protease from *Bacillus lentus* are found in the cited positions: S3, V4, G61, S154, A188, V193, V199, and L211. The amino acids 3T, 4I, 61A, 154D, 154E, 211D, 211G and 211E are particularly preferred, in so far as the corresponding positions in a protease to be inventively added are not already occupied by one of these preferred amino acids. The substitutions 3T and 4I, for example, confer a stabilizing effect to the molecule and lead to an improved storage stability and cleaning power of the protease and hence to an improved cleaning power of an inventive liquid washing or cleaning agent that comprises the protease.

If one or more of the abovementioned amino acids are realized at the respective position, then in addition to position 99, further sequence deviations from SEQ ID NO: 1 ensue, as SEQ ID NO: 1 possesses another amino acid in the respective position. Depending on the number of sequence deviations from SEQ ID NO: 1, there results different maximum identity values that a protease to be inventively added can have to SEQ ID NO: 1, even if it were concordant with SEQ ID NO: 1 in all other amino acids. This situation is to be taken into account in each individual case for every possible combination of the proposed amino acids and moreover is also dependent on the length of the amino acid sequence of the protease. For example, the maximum identity with one, two, three, four, five, six, seven, eight or nine sequence modifications is 99.63%, 99.26%, 98.88%, 98.51%, 98.14%, 97.77%, 97.40%, 97.03% or 96.65% for an amino acid sequence length of 269 amino acids, and 99.64%, 99.27%, 98.91%, 98.55%, 98.18%, 97.82%, 97.45%, 97.09% or 96.73% for an amino acid sequence length of 275 amino acids.

The identity of nucleic acid or amino acid sequences is determined by a sequence comparison. This comparison is made by aligning similar sequences in the nucleotide sequences or amino acid sequences with one another. This sequence comparison is preferably carried out based on the BLAST algorithm that is established in the prior art and usually used (see for example Altschul, S. F., Gish, W., Miller, W., Myers, E. W. & Lipman, D J. (1990) “Basic local alignment search tool.” J. Mol. Biol. 215: 403-410, and Altschul, Stephan F., Thomas L. Madden, Alejandro A.

Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pp. 3389-3402) and does so principally by aligning similar sequences of nucleotides or amino acids in the nucleotide sequences or amino acid sequences with one another. A tabular assignment of the positions is called the alignment. Another algorithm that is available from the prior art is the FASTA algorithm. Sequence alignments, particularly multiple sequence alignments, are usually created with computer programs. The Clustal series are frequently used (see for example Chenna et al. (2003): Multiple sequence alignment with the Clustal series of programs, Nucleic Acid Research 31, 3497-3500), T-Coffee (see, for example Notredame et al. (2000): T-Coffee: A novel method for multiple sequence alignments. J. Mol. Biol. 302, 205-217) or programs that are based on these programs or algorithms. In the context of the present invention, sequence comparisons and alignments are preferably created with the computer program Vector NTI® Suite 10.3 (Invitrogen Corporation, 1600 Faraday Avenue, Carlsbad, California, USA) with the standard default parameters.

A comparison of this type allows a statement to be made of the similarity of the compared sequences to one another. It is usually expressed in percent identity, i.e. in the fraction of the identical nucleotides or amino acid groups to the same or in an alignment to one another in corresponding positions. The wider term "homology" for amino acid sequences takes into consideration conserved amino acid exchanges, i.e. amino acids with similar chemical activity, as they exercise mostly similar activities or functions within the protein. Consequently, the similarity of the compared sequences can also be expressed as percent homology or percent similarity. Identity and/or homology data can be gathered for complete polypeptides or genes or only for individual areas. Homologous or identical areas of various nucleic acid or amino acid sequences are therefore defined by matches in the sequences. They often possess the same or similar functions. They can be small and include only a few nucleotides or amino acids. It is frequently the case that such small areas execute essential functions for the total activity of the protein. Consequently, it can be worthwhile to obtain sequence matches only for individual, optionally small areas. However, when not otherwise stated, identity or homology data in the present application refer to the total length of the relevant listed nucleic acid or amino acid sequence.

In another embodiment of the subject matter of this invention, the washing or cleaning agent is wherein the protease contains an amino acid sequence that is identical to the amino acid sequence listed in the SEQ ID NO: 1 as stated above and which is obtained or is obtainable from a protease according to SEQ ID NO: 1 by one or more conservative amino acid substitutions, wherein the protease at position 99 still possesses one of the amino acids designated for this position as described above. The term "conservative amino acid substitution" means the exchange (substitution) of one amino acid residue for another amino acid residue, wherein this substitution does not lead to a change in the polarity or charge at the position of the exchanged amino acid, e.g. the substitution of a non-polar amino acid residue for another non-polar amino acid residue. In the context of the invention, conservative amino acid substitutions include for example: G=A=S, I=V=L=M, D=E, N=Q, K=R, Y=F, S=T, G=A=I=V=L=M=Y=F=W=P=S=T.

In another embodiment of the invention, a washing or cleaning agent according to the invention is wherein its cleaning power also corresponds to at least that of a washing or cleaning agent that includes a protease that contains an amino acid sequence that corresponds to the amino acid sequence listed in SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, particularly preferably that in SEQ ID NO: 2. The cleaning power is determined in a wash system that comprises a cellulase-containing washing agent in a dose between 2.0 and 9.0 grams per liter wash liquor as well as the protease, wherein the proteases to be compared are added in the same concentration (based on active protein) and the cleaning power is determined against one or more of the soils blood-milk/ink on cotton, whole egg/pigment on cotton, peanut oil-pigment/ink on polyester/cotton and grass on cotton, especially against one or more of the soils

- Blood-milk/ink on cotton: product no. C-05 available from CFT (Center For Testmaterials) B.V. Vlaardingen, Netherlands
- Whole egg/pigment (whole egg/soot) on cotton: product no. 10N obtainable from the company wfk Testgewebe GmbH; Brüggen-Bracht, Germany, or product C-S-37 available from CFT (Center For Testmaterials) B.V. Vlaardingen, Netherlands
- Peanut oil-pigment/ink on polyester/cotton: product no. PC-10 obtainable from CFT (Center For Testmaterials) B.V. Vlaardingen, Netherlands
- Grass on cotton, product no. 164 obtainable from the Eidgenössische Material- and Prüfanstalt (EMPA) Testmaterialien AG, St. Gallen (Switzerland), by measuring the degree of whiteness of the washed fabrics, wherein the washing process lasts for at least 30 minutes, optionally 60 minutes, at a temperature of 20° C. and the water hardness of the water is between 15.5 and 16.5 (German hardness).

The washing agent for the wash system is a liquid washing agent, formulated as follows (all figures in weight percent): 0.3-0.5% xanthane, 0.2-0.4% defoamer, 6-7% glycerin, 0.3-0.5% ethanol, 4-7% FAEOS (fatty alcohol ether sulfate), 24-28% non-ionic surfactants, 1% boric acid, 1-2% sodium citrate (dihydrate), 2-4% soda, 14-16% coconut fatty acids, 0.5% HEDP (1-hydroxyethane-(1,1-diphosphonic acid)), 0-0.4% PVP (polyvinyl pyrrolidone) 0-0.5% optical brightener, 0-0.001% % colorant, 0.0002-0.06% cellulase (active protein), preferably Ecostone N400® (cellulase preparation from the AB Enzymes company), residue demineralized water. The protease is incorporated in a concentration of 0.001-0.1%, preferably 0.01 to 0.06%, in the washing agent, based on the active protein. The liquid washing agent is preferably dosed between 2.0 and 9.0, preferably between 3.0 and 8.2, between 4.0 and 7.5 and particularly preferably 4.7 grams per liter of wash liquor.

The washing is preferably carried out in a pH range between pH 8 and pH 10.5, preferably between pH 8 and pH 9. Neither the protease activity nor the cellulase activity in the wash liquor is equal to zero at the beginning of the wash.

The whiteness degree, i.e. the brightening of the soils as a measure of the cleaning power, is determined with optical measurement methods, preferably photometrically. A suitable apparatus for this is the Minolta CM508d spectrometer, for example. The apparatuses used for the measurement are normally calibrated with a white standard, preferably with a white standard that was delivered with the apparatus.

In another embodiment of the invention, a washing or cleaning agent according to the invention is wherein its storage stability also corresponds to at least that of a washing or cleaning agent that includes a protease that contains an amino acid sequence that corresponds to the amino acid sequence listed in SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, particularly preferably that in SEQ ID NO: 2. Such storage stability exists when the washing or cleaning agent according to the invention exhibits an equal or higher cellulose activity after storage for eight weeks at 30° C. than the washing or cleaning agent used for comparison, wherein the inventive agent only differs by the comprised protease from the washing or cleaning agent used for comparison.

The agent used for the comparison is particularly preferably a liquid washing agent with the following composition (all amounts in weight percent): 0.3-0.5% Xanthane gum, 0.2-0.4% defoamer, 6-7% glycerin, 0.3-0.5% ethanol, 4-7% FAEOS (fatty alcohol ether sulfate), 24-28% non-ionic surfactants, 1% boric acid, 1-2% sodium citrate (dihydrate), 2-4% soda, 14-16% coconut fatty acids, 0.5% HEDP (1-hydroxyethane-(1,1-diphosphonic acid)), 0-0.4% PVP (polyvinyl pyrollidone), 0-0.05% optical brightener, 0-0.001% colorant, 0.0002-0.06% cellulase (of active protein), preferably Ecostone N400® (cellulase preparation from the AB Enzymes company), remainder demineralized water. The protease is incorporated in the washing agent in a concentration of 0.001-0.1%, preferably 0.01 to 0.06%, based on the active protein.

At the beginning of the storage both agents to be compared exhibit the same initial cellulolytic activity, comprise the protease in the same concentration relative to active enzyme, and both agents are treated in the same manner. The proteolytic activity in the agents is determined based on the release of the chromophore para-nitroaniline (pNA) from the substrate suc-AAPF-pNA, and their cellulolytic activity is determined as described previously. The initial activities for the protease and the cellulase in each agent are not equal to zero.

The addition of the cellulase at equal activity and the equal concentration of the proteases, relative to active protein, ensure that even for any possible divergence in the ratios of active substance to total protein (the specific activity value), the true enzymatic properties are compared.

In the context of the present invention, unless otherwise stated, reference is made to the weight of the liquid washing agent, i.e. the data are based on its weight.

Numerous proteases and especially subtilisins are formed as a so-called pre-protein, i.e. together with a pro-peptide and a signal peptide, wherein the function of the signal peptide usually consists in ensuring the elimination of the protease from the cell that produces it into the periplasma or into the medium surrounding the cell, and the pro-peptide is usually required for the correct folding of the protease. The signal peptide and the pro-peptide are generally in the N-terminal part of the pre-protein. Under natural conditions the signal peptide is cleaved from the remaining protease by a signal peptidase. The correct final folding of the protease then occurs supported by the pro-peptide. The protease is then in its active form and cleaves the pro-peptide itself. After cleavage of the propeptide, the mature protease, especially subtilisin, then performs its catalytic activity in the absence of the originally present N-terminal amino acids. For technical applications in general and especially in the context of the invention, the mature proteases, i.e. the enzymes processed after their production, are preferred over the pre-proteins. Furthermore, the proteases can be modified from the cells producing them after the production of the polypeptide chain, for example by the attachment of sugar molecules, by formylations, aminations, etc. Such modifications are post-translational modifications and can, although do not have to, exert an influence on the function of the protease.

Furthermore, the mature protease can also be shortened at its N-terminal and/or C-terminal end, such that a shortened protease in comparison to SEQ ID NO: 1 or SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, i.e. a fragment, is comprised in the washing or cleaning agent according to the invention. In this case all identity data refer to that region, in which the fragment in question is matched in an alignment SEQ ID NO: 1. However, in each case the fragment in question contains that position that is matched to the position 99 in an alignment with SEQ ID NO: 1, and possesses a corresponding amino acid at this position.

Advantageously it also contains one or more of the additional previously described positions and possesses there a corresponding amino acid. Furthermore, such a fragment is proteolytically active. In this regard, a further preferred fragment contains an amino acid sequence that over a length of at least 50 or at least 60, 70, 80, 90, 100, 110, 120, 130, 140, 150, 160, 170, 180, 190, 200, 210, 220, 230, 240, 250, 260, 265, 266, 267 or 268 connected amino acid positions matches SEQ ID NO: 1 or SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, subject to the abovementioned amino acids for the position 99 and optionally also for the positions 3 and/or 4 and/or 61 and/or 154 and/or 188 and/or 193 and/or 199 and/or 211. The cleaning power and/or storage stability of an inventive washing or cleaning agent with such a fragment corresponds to at least that of a washing or cleaning agent that includes a protease that contains an amino acid sequence that corresponds to the amino acid sequence listed in SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, each determined as listed above.

Another subject matter of the invention is a liquid washing or cleaning agent, containing (a) a protease that is selected from the group consisting of a. protease containing an amino acid sequence according to SEQ ID NO: 2 or SEQ ID NO: 3 or SEQ ID NO: 4 or SEQ ID NO: 5 or SEQ ID NO: 6 or SEQ ID NO: 7 or SEQ ID NO: 8;

b. protease that contains a changed amino acid sequence in at least one position in SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, wherein the change in the count according to SEQ ID NO: 1 is selected from the group consisting of:

i. threonine at position 3 (3T), ii. isoleucine at position 4 (4I), iii. alanine, threonine or arginine at position 61 (61A, 61T or 61R), iv. aspartic acid or glutamic acid at position 154 (154D or 154E), v. proline at position 188 (188P), vi. methionine at position 193 (193M), vii. isoleucine at position 199 (199I), viii. aspartic acid, glutamic acid or glycine at position 211 (211D, 211E or 211G), ix. combinations of the amino acids (i) to (viii);

(b) a cellulase.

These proteases are quite particularly preferably incorporated in a liquid washing or cleaning agent according to the invention. Starting from SEQ ID NO: 1 they are obtained by substituting the amino acid arginine at position 99 by the amino acid glutamic acid (E) or aspartic acid (D) or the amino acid asparagine (N) or glutamine (Q) or the amino acid alanine (A) or glycine (G) or serine (S) in the count according to SEQ ID NO: 1. These amino acid sequences are listed in the sequence protocol as the SEQ ID NO: 2, SEQ ID NO: 3, SEQ ID NO: 4, SEQ ID NO: 5, SEQ ID NO: 6, SEQ ID NO: 7 and SEQ ID NO: 8. Furthermore, these proteases can possess, in addition to the amino acid provided for position 99, one or more of the abovementioned amino acids in the positions 3, 4, 61, 154, 188, 193, 199 and 211, to match an alignment with SEQ ID NO: 1 and consequently in the count according to SEQ ID NO: 1. The cited amino acids for these positions also produce further advantageous properties and/or even reinforce already existing properties with these proteases. In particular they bring about an increase in the proteolytic activity and/or in the stability of the protease in a liquid washing or cleaning agent or in the wash liquor formed by this washing or cleaning agent. All the above embodiments—where applicable—correspondingly apply for these particularly preferred proteases.

An agent according to the invention comprises the protease with increasing preference in an amount of $1\times10^{-8}$ to 5 wt %, of 0.0001 to 1 wt %, of 0.0005 to 0.5 wt %, of 0.001 to 0.1 wt % and particularly preferably 0.001 to 0.06 wt %, based on active protein. An agent according to the invention comprises the cellulase with increasing preference in an amount of $1\times10^{-8}$ to 5 wt %, of 0.0001 to 1 wt %, of 0.00005 to 0.5 wt %, of 0.0001 to 0.1 wt % and particularly preferably 0.0001 bis 0.065 wt %, based on active protein. The protein concentration can be determined using known methods, for example the BCA Process (bicinchoninic acid; 2,2'-biquinolyl-4,4'-dicarboxylic acid) or the biuret process (A. G. Gornall, C. S. Bardawill and M. M. David, J. Biol. Chem., 177 (1948), pp. 751-766). In this regard, the active protein concentration is determined by titrating the active centers in the presence of a suitable irreversible inhibitor (for proteases, phenyl methyl sulfonyl fluoride (PMSF) for example) and measuring the residual activity (see M. Bender et al., J. Am. Chem. Soc. 88, 24 (1966), pp. 5890-5913).

The protease and/or the cellulase can also be adsorbed on carriers and/or embedded in encapsulants, in order to protect them against premature decomposition. In the wash liquor, i.e. under conditions of use, the enzyme is then released and can develop its catalytic activity.

In another embodiment of the invention, the washing or cleaning agent additionally includes a component that is selected from i. an anionic and/or polyanionic substance, and/or
ii. a cationic and/or polycationic substance, and/or
iii. a substance that possesses hydroxyl and/or polyhydroxyl group(s).

It was determined that the addition of such substances further improves the cleaning power of washing and cleaning agents, particularly liquid washing or cleaning agents that comprise proteases and cellulases, especially those as described above, in particular at comparatively low temperatures, especially between 10° C. and 50° C., between 10° C. and 40° C., between 10° C. and 30° C. and/or between 20° C. and 40° C. In particular when combined with an inventively incorporable protease, there occurs a synergistic effect, above all in regard to the removal of at least one protease-sensitive soil, especially one such as is listed above.

The substances listed under i. above concern anionic or polyanionic substances, i.e. these substances carry at least one and preferably a plurality of negative charges. They preferably concern a polymer containing at least one negatively charged monomer, preferably a plurality of negatively charged monomers. Accordingly, this inventively preferred polymer is a negatively charged polymer. Exemplary preferred are polymers of organic acids or their salts, especially polyacrylates and/or polysugar acids and/or polyacrylate copolymers and/or polysugar copolymers. In this regard, further preferred compounds are polyacrylic sulfonates or polycarboxylates and their salts, copolymers or salts of the copolymers.

Exemplary particularly preferably added substances are Acusol 587D (polyacrylic sulfonate; Rohm & Haas/Dow Chemical), Acusol 445N (polycarboxylate sodium salt; Rohm & Haas/Dow Chemical), Acusol 590 (polyacrylate copolymer; Rohm & Haas/Dow Chemical), Acusol 916 (polyacrylate sodium salt; Rohm & Haas/Dow Chemical), Sokalan CP42 (modified polycarboxylate sodium salt; BASF), Sokalan PA 30CL (polycarboxylate sodium salt; BASF), Dequest P 9000 (polymaleic acid; Thermphos), alginic acid, poly-2-acrylamido-2-methyl-1-propane sulfonic acid, poly-4-styrene sulfonic acid co-maleic acid sodium salt, polyacrylamide co-acrylic acid sodium salt, polymethacrylic acid sodium salt, polymethyl vinyl ether-alt-maleic acid or polyvinylsulfonic acid sodium salt.

The substances listed under ii. concern cationic or polycationic substances, i.e. these substances carry at least one and preferably a plurality of positive charges. They preferably concern a polymer containing at least one positively charged monomer, preferably a plurality of positively charged monomers. Accordingly, this inventively preferred polymer is a positively charged polymer. Exemplary preferred compounds in this regard are salts of the polyamines, polyethylene imines or their copolymers, salts of the polyallylamines, salts of the polydiallyldimethylammonium compounds or poly(acrylamide-co-diallyldimethylammonium compounds.

The substances listed under iii. concern substances that carry at least one hydroxyl and/or polyhydroxyl group and preferably possess a plurality of hydroxyl and/or polyhydroxyl groups. In this regard, polyvinyl alcohols, for example are preferred, for example those that are available under the trade name Mowiol (Kremer Pigmente GmbH & Co. KG).

At this point, it is expressly pointed out that an actual substance can belong to one or more of the previously cited groups i. to iii. For example it can concern an anionic polymer that possesses one or more hydroxyl and/or polyhydroxyl group(s). A substance of this type then belongs to the groups i. and iii. Likewise, a cationic polymer that possesses one or more hydroxyl and/or polyhydroxyl group(s) belongs to the groups ii. and iii.

In the context of the present invention, derivatives of the abovementioned substances belonging to i. ii. or iii. can likewise be added. In the context of the present application, a derivative is understood to mean a substance that, starting from one of the previously cited substances, is chemically modified, for example by the conversion of a side chain or by covalently bonding another compound onto the substance. Such a compound can concern for example low molecular weight compounds such as lipids or mono-, oligo- or polysaccharides or amines or amine compounds. Moreover, the substance can be glycolyzed, hydrolyzed, oxidized, N-methylated, N-formylated, N-acetylated or comprise methyl, formyl, ethyl, acetyl, t-butyl, anisyl, benzyl, trifluoroacetyl, N-hydroxysuccinimide, t-butyloxycarbonyl, benzoyl, 4-methylbenzyl, thioanicyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethylchroman-6-sulfonyl. Likewise, a derivative is understood to mean the covalent or non-covalent bonding of the substance onto a macromolecular carrier, just as also a non-covalent inclusion in suitable macromolecular cage structures. Coupling with other macromolecular compounds, such as for example polyethylene glycol, can also be carried out. Further preferred chemical modifications are the modification of one or more of the chemical groups —COOH, —OH, =NH, —$NH_2$ —SH to —COOR, —OR, —NHR, —NR2, —NHR, —NR, —SR; wherein:

R is —CH═CH—R2, —C≡C—R2, —C(R2)=$CH_2$, —C(R2)=C(R3), —CH═NR2, —C(R2)=N—R3, a 4-7 carbon ring system with or without substitution, a 4-7 nitrogen heterocycle with or without substitution, or a $C_2$ to $C_8$ carbon chain with 1 to 5 double or triple bonds with substitutions selected from R1, R2, or R3, wherein —R1 is H, —R, —$NO_2$, —CN, halide substituent, —$N_3$, —C1-8 alkyl, —$(CH_2)_n CO_2$R2, —C2-8 alkenyl-$CO_2$R2, —$O(CH_2)_n CO_2$R2, —C(O)NR2R3, —P(O)$(OR2)_2$, alkyl substituted tetrazol-5-yl, —$(CH_2)_n$O$(CH_2)_n$ aryl, —NR2R3, —$(CH_2)_n$OR2, —$(CH_2)_n$SR2, —N(R2)C(O)R3, —S($O_2$)NR2R3, —N(R2)S($O_2$)R3, —$(CHR2)_n$NR2R3, —C(O)R3, $(CH_2)_n$N(R3)C(O)R3, —N(R2)CR2R3, substituted or unsubstituted $(CH_2)_n$-cycloalkyl, substituted or unsubstituted $(CH_2)_n$-phenyl, or -ring; wherein n is a number greater than 1;

—R2 is H, halide substituent, -alkyl, -haloalkyl, —$(CH_2)_n$-phenyl, —($CH_2$)1-3-biphenyl, —($CH_2$)1-4-Ph-N($SO_2$—C1-2-alkyl)2, —CO(CHR1)n-OR1, —(CHR1)n-heterocycle, —(CHR1)n-NH—CO—R1, —(CHR1)n-NH—$SO_2$R1, —(CHR1)n-Ph-N($SO_2$—C1-2-alkyl)2, —(CHR1)n-C(O)(CHR1)-NHR1, —(CHR1)n-C(S)(CHR1)-NHR1, —(CH2)nO(CH2)n$CH_3$, —$CF_3$, —$C_2$-$C_5$ acyl, —(CHR1)nOH, —(CHR1)nCO2R1, —(CHR1)n-O-alkyl, —(CHR1)n-O—(CH2)n-O-alkyl, —(CHR1)n-S-alkyl, —(CHR1)n-S(O)-alkyl, —(CHR1)n-S($O_2$)-alkyl, —(CHR1)n-S($O_2$)—NHR3, —(CHR3)n-$N_3$, —(CHR3)nNHR4, a $C_2$ to $C_8$ chain alkene chain with 1 to 5 double bonds, a $C_2$ to $C_8$ chain alkyne chain with 1 to 5 triple bonds, substituted or unsubstituted —(CHR3)n heterocycle, substituted or unsubstituted saturated or unsaturated —(CHR3)n cycloalkyl; wherein n is a number greater than 1 and R1 and R3 can be the same or different;

—R3 is H, —OH, —CN, substituted alkyl, —$C_2$ to $C_8$ alkenyl, substituted or unsubstituted cycloalkyl, —N(R1)R2, saturated or unsaturated $C_5$ to $C_7$ heterocycle or heterobicycle of 4 to 7 carbon atoms, —NR1, —NR2, —NR1 R2 consisting of a saturated or unsaturated heterocycle or a heterobicycle of 4 to 7 carbon atoms;

—R4 is H, —($CH_2$)nOH, —C(O)OR5, —C(O)SR5, —($CH_2$)nC(O)NR6R7, —O—C(O)—O—R6, an amino acid or a peptide; wherein n is a number between 0 and 4;

—R5 is H,

—R6 is —C(R7)-($CH_2$)n-O—C(O)—R8, —($CH_2$)n-C(R7)-O—C(O)R8, —($CH_2$)n-C(R7)-O—C(O)—O—R8, or —C(R7)-($CH_2$)n-O—C(O)—O—R8; wherein n is a number between 0 and 4; and —R7 and R8 are each H, alkyl, substituted alkyl, aryl, substituted aryl, alkenyl, substituted alkenyl, alkynyl, substituted alkynyl, heterocyclic, substituted heterocyclic, alkylaryl, substituted alkylaryl, cycloalkyl, substituted cycloalkyl, or $CH_2CO_2$alkyl, wherein R7 and R8 can be the same or different.

It is also inventively possible to employ all possible combinations of the previously cited substances that belong to i., ii. or iii. and/or their derivatives.

A liquid washing or cleaning agent according to the invention can be used as such or after dilution with water, especially for cleaning fabrics and/or hard surfaces. Such a dilution can be produced easily, in that a measured amount of the agent is diluted in an additional amount of water in defined weight ratios of agent:water, and optionally with shaking, in order to ensure a uniform distribution of the agent in the water. Possible weight or volume ratios for the dilutions are from 1:0 agent:water to 1:10000 or 1:20000 agent:water, preferably from 1:10 to 1:2000 agent:water.

All liquid or free-flowing dosage forms can be used as the liquid washing or cleaning agent. In the context of the present application, "free-flowing" is understood to mean preparations that are pourable and can have viscosities up to several 10 000 mPas. The viscosity can be measured using standard methods (for example using a Brookfield-Viscosimeter LVT-II at 20 rpm and 20° C., spindle 3) and is preferably in the range of 5 to 10 000 mPas. Preferred agents have viscosities from 10 to 8000 mPas, particularly preferably from 120 to 3000 mPas. In the context of the present invention, a liquid washing or cleaning agent can therefore also be in gel form or in paste form, it can be a homogenous solution or suspension, it can be sprayable for example or be packaged in other usual dosage forms. Washing agents include all conceivable types of washing agents, especially washing agents for fabrics, carpets or natural fibers. They can be provided for manual and/or automatic use. The washing agents further include washing auxiliaries that in the course of a manual or automatic fabric wash are metered into the actual washing agent in order to achieve another effect. The cleaning agents include all agents, likewise in any cited dosage forms, for cleaning and/or disinfecting hard surfaces, manual and automatic dishwasher detergents, carpet cleaners, scouring agents, glass cleaners, WC-fragrant rinses, etc. Fabric pre- and after-conditioners are on the one hand those materials that are brought into contact with the washing prior to the actual wash, for example in order to partially dissolve intractable soils, and on the other hand those materials that in a step that follows on from the actual fabric wash, to confer additional desirable properties to the washing, such as a pleasant touch, absence of creasing or a low residual static charge. The last mentioned agents include inter alia the fabric softeners. Disinfectants are for example hand disinfectants, surface disinfectants and instrument disinfectants which can also be in any cited dosage form.

In another preferred embodiment of the invention, the washing or cleaning agent contains at least one further ingredient, in particular one that is selected from the group consisting of phosphonate, surfactant, builder, non-aqueous solvent, acid, water-soluble salt, thickener as well as combinations thereof.

Phosphonates are salts and organic compounds, especially esters, of phosphonic acid. The salts exist as primary (M'$H_2PO_3$ or HP(O)(OH)(OM')) and secondary ($M'_2HPO_3$ or HP(O)$(OM')_2$) phosphonates, wherein M' stands for a monovalent metal. These inorganic phosphonates are also called primary or secondary phosphites. Inorganic phosphonates result for example by reacting phosphonic acid HP(O)$(OH)_2$, in particular the stable tautomeric form of the phosphorous acid with one (primary) or two (secondary) equivalents of base, for example alkali metal hydroxide. In the context of the present invention, organic P-substituted phosphonates that possess a phosphorus-carbon bond are preferred (organophosphorus compounds). Their general formula is $R1P(O)(OR2)_2$, with R1 and/or R2=alkyl, aryl or H, wherein the alkyl or aryl groups are further substituted or can carry additional chemical groups. Organic P-substituted phosphonates are formed for example by the Michaelis-Arbusov Reaction. Many of these phosphonates are soluble in water. Some industrially important phosphonates carry additional amino group(s) of the type $NR—(CH_2)_x—PO(OH)_2$ (R=alkyl, aryl or H). Some of these amino phosphonates are structurally similar to complexants such as EDTA, NTA or DTPA and have a similar function. In the context of the present invention, particularly preferred phosphonates especially include organophosphonates such as for example 1-hydroxyethane-1,1-diphosphonic acid (HEDP), am inotri (methylene phosphonic acid) (ATMP, also called amino-tris (methylene phosphonic acid) or nitrolotris(methylene phosphonic acid) (NTMP)), diethylenetriaminepenta(methylene phosphonic acid) (DTPMP or DETPMP or DTPNT), ethylenediaminetetra(methylene phosphonic acid) (EDTMP, also called ethylenediaminetetra(methylene phosphonic acid) and 2-phosphonobutane-1,2,4-tricarboxylic acid (PBS-AM, also called 2-phosphonobutane-1,2,4-tricarboxylic acid or 3-carboxy-3-phosphonoadipic acid), which are mainly added in the form of their ammonium or alkali metal salts. Diethylenetriaminepenta(methylene phosphonic acid) sodium salt is particularly preferred. Such a phosphonate is available for example under the trade name Dequest® 2066 (Thermphos company).

The phosphonate is preferably comprised in the washing or cleaning agent in an amount of 0.01 to 2.5 wt % and increasingly preferably from 0.02 to 2 wt %, 0.03 to 1.5 wt % and in particular 0.05 to 1 wt %.

Anionic, non-ionic, zwitterionic and/or amphoteric surfactants can be added as the surfactant(s). Mixtures of anionic and non-ionic surfactants are preferred from the industrial application viewpoint. The total surfactant content of the liquid washing or cleaning agent is preferably below 60 wt % and particularly preferably below 45 wt %, based on the total liquid washing or cleaning agent.

Suitable non-ionic surfactants include alkoxylated fatty alcohols, alkoxylated fatty acid alkyl esters, fatty acid amides, alkoxylated fatty acid amides, polyhydroxyfatty acid amides, alkylphenol polyglycol ethers, amine oxides, alkyl polyglucosides and mixtures thereof.

Preferred non-ionic surfactants are alkoxylated, advantageously ethoxylated, particularly primary alcohols preferably containing 8 to 18 carbon atoms and, on average, 1 to 12 moles of ethylene oxide (EO) per mole of alcohol, in which the alcohol group may be linear or, preferably, methyl-branched in the 2-position or may contain e.g. linear and methyl-branched groups in the form of the mixtures typically present in Oxo alcohol residues. In particular, however, alcohol ethoxylates with linear alcohol groups of natural origin with 12 to 18 carbon atoms, for example from coco-, palm-, tallow- or oleyl alcohol, and an average of 2 to 8 EO per mole alcohol are preferred. Exemplary preferred ethoxylated alcohols include $C_{12-14}$ alcohols with 3 EO or 4EO, $C_{9-11}$ alcohols with 7 EO, $C_{13-15}$ alcohols with 3 EO, 5 EO, 7EO or 8 EO, $C_{12-18}$ alcohols with 3 EO, 5 EO or 7 EO and mixtures thereof, such as mixtures of $C_{12-14}$ alcohol with 3 EO and $C_{12-18}$ alcohol with 5 EO. The cited degrees of ethoxylation constitute statistically average values that can be a whole or a fractional number for a specific product. Preferred alcohol ethoxylates have a narrowed homolog distribution (narrow range ethoxylates, NRE). In addition to these non-ionic surfactants, fatty alcohols with more than 12 EO can also be used. Examples of these are tallow fatty alcohol with 14 EO, 25 EO, 30 EO or 40 EO. Also, non-ionic surfactants that comprise the EO and PO groups together in the molecule are employable according to the invention. Further suitable is also a mixture of a (highly) branched ethoxylated fatty alcohol and a linear ethoxylated fatty alcohol, such as for example a mixture of a $C_{16-18}$ fatty alcohol with 7 EO and 2-propylheptanol with 7 EO. The washing, cleaning, post-treatment or auxiliary washing agent particularly preferably comprises a $C_{12-18}$ fatty alcohol with 7 EO or a $C_{13-15}$ Oxo alcohol with 7 EO as the non-ionic surfactant.

The content of non-ionic surfactants in the washing or cleaning agent is preferably 3 to 40 wt %, advantageously 5 to 30 wt % and particularly 7 to 20 wt %, in each case based on the total washing or cleaning agent.

In addition to the non-ionic surfactants, the washing or cleaning agent can also comprise anionic surfactants. Sulfonates, sulfates, soaps, alkyl phosphates, anionic silicosurfactants and mixtures thereof are preferably employed as the anionic surfactant.

Suitable surfactants of the sulfonate type are, advantageously $C_{9-13}$ alkylbenzene sulfonates, olefin sulfonates, i.e. mixtures of alkene and hydroxyalkane sulfonates and disulfonates, as are obtained, for example, from $C_{12-18}$ monoolefins having a terminal or internal double bond, by sulfonation with gaseous sulfur trioxide and subsequent alkaline or acidic hydrolysis of the sulfonation products. The esters of $C_{12-18}$ alkane sulfonates and the esters of α-sulfofatty acids (ester sulfonates), e.g. the α-sulfonated methyl esters of hydrogenated coco-, palm nut- or tallow acids are likewise suitable.

Preferred alk(en)yl sulfates are the alkali metal and especially the sodium salts of the sulfuric acid half-esters derived from the $C_{12}$-$C_{18}$ fatty alcohols, for example from coconut butter alcohol, tallow alcohol, lauryl, myristyl, cetyl or stearyl alcohol or from $C_{10}$-$C_{20}$ Oxo alcohols and those half esters of secondary alcohols of these chain lengths. The $C_{12}$-$C_{16}$ alkyl sulfates and $C_{12}$-$C_{15}$ alkyl sulfates as well as $C_{14}$-$C_{15}$ alkyl sulfates are preferred on the grounds of washing performance. 2,3-Alkyl sulfates are also suitable anionic surfactants.

Sulfuric acid mono-esters derived from straight-chain or branched $C_{7-21}$ alcohols ethoxylated with 1 to 6 moles ethylene oxide are also suitable, for example 2-methyl-branched $C_{9-11}$ alcohols with an average of 3.5 mole ethylene oxide (EO) or $C_{12-18}$ fatty alcohols with 1 to 4 EO.

Soaps are also preferred anionic surfactants. Saturated and unsaturated fatty acid soaps are suitable, such as the salts of lauric acid, myristic acid, palmitic acid, stearic acid, (hydrogenated) erucic acid and behenic acid, and especially soap mixtures derived from natural fatty acids such as coconut oil fatty acid, palm kernel oil fatty acid, olive oil fatty acid or tallow fatty acid.

The anionic surfactants, including the soaps, can be present in the form of their sodium, potassium or magnesium or ammonium salts. The anionic surfactants are preferably present in the form of their sodium salts. Further preferred counter ions for the anionic surfactants are also the protonated forms of choline, triethylamine or methylethylamine.

The content of anionic surfactants in a washing or cleaning agent is 1 to 40 wt %, advantageously 5 to 30 wt % and quite particularly preferably 10 to 25 wt %, in each case based on the total washing or cleaning agent.

Silicates, aluminum silicates (particularly zeolites), carbonates, salts of organic di- and polycarboxylic acids as well as mixtures of these materials can be particularly cited as builders that are comprised in the washing or cleaning agents.

Organic builders that can be present in the washing or cleaning agent are, for example, the polycarboxylic acids usable in the form of their sodium salts, polycarboxylic acids in this context being understood to be carboxylic acids that carry more than one acid function. These include, for example, citric acid, adipic acid, succinic acid, glutaric acid, malic acid, tartaric acid, maleic acid, fumaric acid, sugar acids, amino carboxylic acids, nitrilotriacetic acid (NTA), methylglycine diacetic acid (MGDA) and their derivatives and mixtures thereof. Preferred salts are the salts of polycarboxylic acids such as citric acid, adipic acid, succinic acid, glutaric acid, tartaric acid, sugar acids and mixtures thereof.

Polymeric polycarboxylates are also suitable as builders. These are for example the alkali metal salts of polyacrylic acid or polymethacrylic acid, for example those with a relative molecular mass of 600 to 750 000 g/mol.

Particularly suitable polymers are polyacrylates, which preferably have a molecular mass of 1000 to 15 000 g/mol. By virtue of their superior solubility, preferred representatives of this group can again be the short-chain polyacrylates, which have molecular weights of 1000 to 10 000 g/mol and particularly preferably 1000 to 5000 g/mol.

Further suitable copolymeric polycarboxylates are particularly those of acrylic acid with methacrylic acid and of acrylic acid or methacrylic acid with maleic acid. In order to improve the water solubility, the polymers can also comprise allyl sulfonic acids as the monomer, such as allyloxybenzene sulfonic acid and methallyl sulfonic acid.

However, soluble builders are preferred, such as for example citric acid, or acrylic polymers with a molecular mass of 1000 to 5000 g/mol are preferably added into the liquid washing or cleaning agents.

The molecular masses mentioned for polymeric polycarboxylates in the context of this specification are weight-average molecular weights Mw of the particular acid form which were fundamentally determined by means of gel permeation chromatography (GPC) using a UV detector. The measurement was carried out against an external polyacrylic acid standard, which provides realistic molecular weight values by virtue of its structural similarity to the investigated polymers. These values differ significantly from the molecular weights measured against polystyrene sulfonic acids as the standard. The molecular masses measured against polystyrene sulfonic acids are generally significantly higher than the molecular masses mentioned in this specification.

These types of organic builders can be comprised as desired in amounts of up to 40 wt %, particularly up to 25 wt % and preferably from 1 wt % to 8 wt %. Amounts close to the cited upper limit are preferably incorporated in pasty or liquid, particularly aqueous compositions.

The washing or cleaning agents according to the invention are liquid and preferably comprise water as the major solvent. In addition, non-aqueous solvents can be added to the washing or cleaning agent. Suitable non-aqueous solvents include monohydric or polyhydric alcohols, alkanolamines or glycol ethers, in so far that they are miscible with water in the defined concentration range. The solvents are preferably selected from ethanol, n-propanol, i-propanol, butanols, glycol, propane diol, butane diol, glycerin, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycolethyl ether, propylenglycolmethyl ether, propylene glycol ethyl ether, propylene glycol propyl ether, dipropylene glycol monomethyl ether, dipropylene glycol monoethyl ether, di-isopropylene glycol monomethyl ether, di-isopropylene glycol monoethyl ether, methoxytriglycol, ethoxytriglycol, butoxytriglycol, 1-butoxyethoxy-2-propanol, 3-methyl-3-methoxybutanol, propylene glycol t-butyl ether, di-n-octyl ether as well as mixtures of these solvents. However, it is preferred that the washing or cleaning agent comprises a polyol as the non-aqueous solvent. In particular, the polyol can include glycerin, 1,2-propane diol, 1,3-propane diol, ethylene glycol, diethylene glycol and/or dipropylene glycol. The washing or cleaning agent particularly preferably comprises a mixture of a polyol and a monohydric alcohol. Non-aqueous solvents can be added to the washing or cleaning agent in amounts between 0.5 and 15 wt %, preferably, however below 12 wt % and.

To adjust a pH resulting from mixing the usual components to a desired level, the agents can comprise acids that are compatible with the system and the environment, particularly citric acid, acetic acid, tartaric acid, malic acid, lactic acid, glycolic acid, succinic acid, glutaric acid and/or adipic acid, but also mineral acids, particularly sulfuric acid, or bases, particularly ammonium hydroxide or alkali metal hydroxides. These types of pH adjustors are preferably comprised in the agents in amounts of not more than 20 wt %, particularly 1.2 wt % to 17 wt %.

In the context of the invention, an agent can additionally comprise one or more water-soluble salts that serve, for example, to adjust the viscosity. In this regard they can be inorganic or organic salts. Here, inorganic salts that can be incorporated are preferably selected from the group that includes colorless water-soluble halides, sulfates, sulfites, carbonates, hydrogen carbonates, nitrates, nitrites, phosphates and/or oxides of the alkali metals, of the alkaline earth metals, of aluminum and/or of transition metals; in addition, ammonium salts can be incorporated. In this regard, halides and sulfates of the alkali metals are particularly preferred; consequently the inorganic salt is preferably selected from the group that includes sodium chloride, potassium chloride, sodium sulfate, potassium sulfate as well as their mixtures. Exemplary organic salts that can be incorporated are colorless water-soluble alkali metal, alkaline earth metal, ammonium, aluminum and/or transition metal salts of carboxylic acids. The salts are preferably selected from the group that includes formate, acetate, propionate, citrate, malate, tartrate, succinate, malonate, oxalate, lactate as well as mixtures thereof.

An agent according to the invention can comprise one or more thickeners to thicken it. The thickener is preferably selected from the group that includes xanthan, guar, carrageenan, agar agar, gellan, pectin, locust bean flour and mixtures thereof. These compounds are also effective thickeners in the presence of inorganic salts. In a particularly preferred embodiment, the washing or cleaning agent comprises xanthan as the thickener, as xanthan thickens effectively even in the presence of high salt concentrations and prevents a macroscopic separation of the continuous phase.

In addition, the thickener stabilizes the continuous surfactant-poor phase and prevents a macroscopic phase separation.

Alternatively, (meth)acrylic acid (co)polymers can also be employed as the thickener. Exemplary suitable acrylic and methacrylic copolymers include the high molecular weight homopolymers of acrylic acid, crosslinked with a polyalkenyl polyether, in particular an allyl ether of saccharose, pentaerythritol or propylene (INCI name according to the "International Dictionary of Cosmetic Ingredients" of "The Cosmetic, Toiletry and Fragrance Association (CTFA)": Carbomer), which are also called carboxyvinyl polymers. Polyacrylic acids of this type are available inter alia under the trade names Polygel® and Carbopol®. In addition, the following acrylic acid copolymers are suitable, for example: (i) copolymers of two or more monomers of the group of the acrylic acid, methacrylic acid and their simple esters, preferably formed with $C_{1-4}$ alkanols (INCI Acrylates Copolymer), which are available for example under the trade names Aculyn®, Acusol® or Tego® Polymer; (ii) crosslinked high molecular weight acrylic acid copolymers, to which belong for example the copolymers of $C_{10-30}$ alkyl acrylates with one or more monomers of the group of acrylic acid, methacrylic acid and their simple esters, preferably formed with $C_{1-4}$ alkanols, crosslinked with an allyl ether of saccharose or of pentaerythritol (INCI Acrylates/$C_{10-30}$ Alkyl Acrylate Crosspolymer) and which are available under the trade name Carbopol®. Further suitable polymers are (meth)acrylic acid (co)polymers of the Sokalan® type.

It can be preferred that the inventive washing or cleaning agent comprises a (meth)acrylic acid (co)polymer in combination with another thickener, preferably xanthan. The washing or cleaning agent can comprise 0.05 to 1.5 wt % and preferably 0.1 to 1 wt % thickener, each based on the total washing or cleaning agent. The amount of added thickener depends in this regard on the type of thickener and the desired degree of thickening.

Liquid or pasty inventive agents in the form of solutions in standard solvents are generally prepared by a simple mixing of the ingredients, which can be added as is or as a solution into an automatic mixer.

Washing or cleaning agents according to the invention can exclusively comprise a protease and a cellulase as described. Alternatively, they can also comprise additional hydrolytic enzymes or other enzymes in a concentration that is appropriate for the activity of the agent. Another subject matter of the invention is illustrated by agents that additionally contain one or more further enzymes, wherein in principle all enzymes found in the prior art for these purposes can be added. All enzymes that can develop a catalytic activity in an agent according to the invention can preferably be incorporated as the additional enzymes, in particular a protease, amylase, cellulase, hemicellulase, mannanase, tannase, xylanase, xanthanase, β-glucosidase, pectinase, carrageenase, perhydrolase, oxidase, oxidoreductase or a lipase, as well as their mixtures. Additional enzymes are each advantageously comprised in the agent in a total amount of $1\times10^{-8}$ to 5 wt % based on the active protein. Each additional enzyme is comprised with increasing preference in agents according to the invention in an amount of $1\times10^{-7}$ to 3 wt %, 0.00001 to 1 wt %, 0.00005 to 0.5 wt %, 0.0001 to 0.1 wt % and particularly preferably 0.0001 to 0.05 wt %, based on active protein. The enzymes particularly preferably exhibit synergistic cleaning powers towards certain soils or stains, i.e. the enzymes comprised in the agent composition mutually support each other in their cleaning power. Such a synergy is quite particularly preferably present between the inventively comprised protease and another enzyme of an agent according to the invention, in particular between the cited protease and the cellulase and/or a lipase and/or a mannanase and/or an amylase and/or a pectinase. Synergistic effects can not only appear between various enzymes but also between one or more enzymes and additional ingredients of the agent according to the invention.

Another subject matter of the invention is represented by the use of an agent according to the invention for removing soils, in particular protease-sensitive and/or cellulase-sensitive soils, on fabrics or hard surfaces, i.e. for cleaning fabrics or hard surfaces. Due in particular to the comprised combination of protease and cellulase, the agents according to the invention can be advantageously used for this purpose in order to eliminate corresponding contamination from fabrics or from hard surfaces. Washing by hand, the manual removal of stains from fabrics or from hard surfaces or the use in connection with an automatic process are exemplary embodiments of this subject matter of the invention. All facts, subject matters and embodiments, which have been described for washing or cleaning agents according to the invention, are also applicable to this subject matter of the invention. Therefore, reference is hereby explicitly made to the disclosure at the appropriate location with the remark that this disclosure is also valid for the preceding use according to the invention.

Another subject matter of the invention is represented by a method for cleaning fabrics or hard surfaces, wherein a washing or cleaning agent according to the invention is used in at least one process step.

These methods include both manual as well as automatic methods, automatic methods being preferred due to their more precise controllability in regard to, for example, the added quantities and contact times. Processes for the cleaning of fabrics are generally those, wherein various cleaning-active substances are applied to the material to be cleaned in a plurality of process steps and, after the contact time, are washed away, or that the material to be cleaned is treated in any other way with a washing agent or a solution or dilution of this agent. The same is true for methods for cleaning all materials other than fabrics, especially hard surfaces. It is possible to add a washing or cleaning agent according to the invention to at least one of the process steps of all conceivable washing or cleaning processes; accordingly, these processes then become embodiments of the present invention. All facts, subject matters and embodiments, which have been described for washing or cleaning agents according to the invention, are also applicable to this subject matter of the invention. Therefore, reference is hereby explicitly made to the disclosure at the appropriate location with the remark that this disclosure is also valid for the preceding method according to the invention.

In a preferred embodiment, the method is wherein the cellulase is present in the washing liquor in a concentration of 0.0000004 to 0.0006 wt %, preferably 0.0000008 to 0.00048 wt %, and/or that the protease is present in the washing liquor in a concentration of 0.00009 to 0.0005 wt %, preferably 0.00015 to 0.00035 wt %, wherein the data are based on active protein in the washing liquor. In another preferred embodiment, the method according to the invention is carried out at a temperature between 10° C. and 50° C., preferably between 10° C. and 40° C. and particularly preferably between 20° C. and 40° C.

Corresponding to the above embodiments, proteases incorporated in agents according to the invention can be advantageously employed in washing and cleaning agents according to the invention as well as in methods, especially washing and cleaning methods. They can therefore be advantageously used in order to provide a proteolytic activity in corresponding agents.

Accordingly, another subject matter is formed by the use of a protease, (a1) that contains an amino acid sequence that is at least 80% identical to the amino acid sequence listed in SEQ ID NO: 1 and that has the amino acid glutamic acid (E) or aspartic acid (D) at position 99 in the count according to SEQ ID NO: 1, or (a2) that contains an amino acid sequence that is at least 80% identical to the amino acid sequence listed in SEQ ID NO: 1 and that has the amino acid asparagine (N) or glutamine (Q) at position 99 in the count according to SEQ ID NO: 1, or (a3) that contains an amino acid sequence that is at least 80% identical to the amino acid sequence listed in SEQ ID NO: 1 and that has the amino acid alanine (A) or glycine (G) or serine (S) at position 99 in the count according to SEQ ID NO: 1, for the provision of a proteolytic activity in a liquid washing or cleaning agent that additionally contains a cellulase.

In another embodiment, this use is wherein the protease further comprises at least one of the following amino acids in the count according to SEQ ID NO: 1:

(a) threonine at position 3 (3T),
(b) isoleucine at position 4 (4I),
(c) alanine, threonine or arginine at position 61 (61A, 61T or 61R),
(d) aspartic acid or glutamic acid at position 154 (154D or 154E),
(e) proline at position 188 (188P),
(f) methionine at position 193 (193M),
(g) isoleucine at position 199 (199I),
(h) aspartic acid, glutamic acid or glycine at position 211 (211D, 211E or 211G),
(i) combinations of the amino acids (a) to (h).

Another subject matter of the invention is formed by the use of a protease that is selected from the group consisting of a. protease containing an amino acid sequence according to SEQ ID NO: 2 or SEQ ID NO: 3 or SEQ ID NO: 4 or SEQ ID NO: 5 or SEQ ID NO: 6 or SEQ ID NO: 7 or SEQ ID NO: 8;
b. protease that contains a changed amino acid sequence in at least one position in SEQ ID NO: 2 or SEQ ID NO: 3 or SEQ ID NO: 4 or SEQ ID NO: 5 or SEQ ID NO: 6 or SEQ ID NO: 7 or SEQ ID NO: 8, wherein the change in the count according to SEQ ID NO: 1 is selected from the group consisting of:

i. threonine at position 3 (3T),
ii. isoleucine at position 4 (4I),
iii. alanine, threonine or arginine at position 61 (61A, 61T or 61R),
iv. aspartic acid or glutamic acid at position 154 (154D or 154E),
v. proline at position 188 (188P),
vi. methionine at position 193 (193M),
vii. isoleucine at position 199 (199I),
viii. aspartic acid, glutamic acid or glycine at position 211 (211D, 211E or 211G),
ix. combinations of the amino acids (i) to (viii);

for the provision of a proteolytic activity in a liquid washing or cleaning agent that additionally contains a cellulase.

All facts, subject matters and embodiments, which have been described for washing or cleaning agents according to the invention, are also applicable to the cited use. Therefore, reference is hereby explicitly made to the disclosure at the appropriate location with the remark that this disclosure is also valid for the preceding uses according to the invention.

EXAMPLE

Determination of the Storage Stability of the Liquid Washing Agent According to the Invention The washing agent base formulations were a) a first liquid washing agent of the following composition (all data in wt %): 0.3-0.5% xanthane, 0.2-0.4% defoamer, 6-7% glycerin, 0.3-0.5% ethanol, 4-7% FAEOS (fatty alcohol ether sulfate), 24-28% non-ionic surfactants, 1% boric acid, 1-2% sodium citrate (dihydrate), 2-4% soda, 14-16% coconut fatty acids, 0.5% HEDP, (1-hydroxyethane-(1,1-diphosphonic acid)), 0-0.4% PVP (polyvinyl pyrrolidone) 0-0.5% optical brightener, 0-0.001% colorant, residue demineralized water. The comprised cellulase was 0.15 wt % Ecostone N400® (cellulase preparation from AB Enzymes company).

b) a second liquid washing agent of the following composition:

| Ingredient | wt % |
|---|---|
| $C_{12-18}$ fatty alcohol with 7 EO | 7.5 |
| Lin. $C_{10}$-$C_{13}$ alkylbenzene sulfonate (Na salt) | 8.5 |
| Cocofatty acid (Na salt) | 14.6 |
| Lauryl ether sulfate with 2 EO (Na salt) | 13.0 |
| Citric acid (Na salt) | 3.1 |
| Boric acid (Na salt) | 1.0 |
| Polyacrylate thickener | 0.4 |
| Propylene glycol | 2.1 |
| silicone defoamer | 0.2 |
| Cellulase preparation Ecostone N400 ® (AB Enzymes) | 0.1 |
| Water | ad 100 |

To the washing agent base formulations were added the following proteases for the various experimental approaches, wherein the data are based on active protein:

Approach 1: Performance improved variant F49 of the protease from *Bacillus lentus* according to WO 95/23221 (Arg at position 99 (99R)): 0.4 mg/ml (0.04 wt %) into the liquid washing agents according to a) and b).

Approach 2: Protease, disclosed in FIG. 2 or SEQ ID NO: 3 of the international patent application WO 03/057713 (Ser at position 99 (99S); identity to SEQ ID NO: 1<80%): 0.4 mg/ml (0.04 wt %) in the liquid washing agent according to a), 0.3 mg/ml (0.03 wt %) in the liquid washing agent according to b).

Approach 3: Protease, containing an amino acid sequence according to SEQ ID NO: 2 (Glu at position 99 (99E)): 0.4 mg/ml (0.04 wt %) in the liquid washing agent according to a), 0.3 mg/ml (0.03 wt %) in the liquid washing agent according to b).

The storage stabilities of the washing agents according to each of the approaches 1, 2 and 3 were tested. The washing agents were stored at a temperature of 30° C. for the relevant time and the respective residual cellulolytic activity determined. The test samples were incubated under defined reaction conditions (100 mM sodium phosphate buffer pH 7.5, 40° C., 15 min) with a substrate (1.25% carboxymethyl cellulose). The reacted under alkaline conditions with p-hydroxybenzoic acid hydrazide (PAHBAH) in the presence of bismuth to afford a yellow dye that was determined photometrically at a wavelength of 410 nm. The quantity of released sugar corresponding to the coloration is a measure of the enzyme activity (see Lever, Anal. Biochem., 1972, 47 & 1977, 81). The measured residual cellulolytic activities are listed in Table 1.

TABLE 1

| Washing | a) | | | b) | | |
|---|---|---|---|---|---|---|
| agent according to | Initial | 4 weeks | 8 weeks | Initial | 4 weeks | 8 weeks |
| Approach 1 | 100% | 42% | 27% | 100% | 33% | 21% |
| Approach 2 | 100% | 36% | 24% | 100% | 42% | 24% |
| Approach 3 | 100% | 46% | 32% | 100% | 49% | 26% |

It is evident that inventive washing agents exhibit a significantly improved residual cellulolytic activity and consequently storage stability in comparison to the washing agents of the approaches 1 and 2.

The invention claimed is:

1. A method of formulating a liquid washing or cleaning agent for storage stability of cellulolytic activity, the method comprising:

(1) mixing, to formulate the liquid washing or cleaning agent:

(a) a protease comprising the amino acid sequence of SEQ ID NO: 2, wherein said amino acid sequence imparts a proteolytic activity to the protease, and wherein the protease imparts a proteolytic activity to the washing or cleaning agent; and (b) a cellulase; and (2) storing the liquid washing or cleaning agent for at least 4 weeks, wherein the liquid washing or cleaning agent exhibits higher cellulolytic activity after storage as compared to a control liquid washing or cleaning agent that is the same liquid washing or cleaning agent but comprises a protease that differs from the protease of (1) (a) solely by having a protease comprising the amino acid arginine (R) at location 99 in the count according to SEQ ID NO: 1;

wherein the liquid washing or cleaning agent exhibits higher cellulolytic activity after storage for 4 weeks at 30° C. as compared to a control liquid washing or cleaning agent that is the same liquid washing or cleaning agent but comprises a protease that differs from the protease of (1) (a) solely by having a protease comprising the amino acid arginine (R) at location 99 in the count according to SEQ ID NO: 1, wherein, at the beginning of such storage, the liquid washing or cleaning agent and the control liquid washing or cleaning agent have the same concentration of protease and the same concentration of cellulase, and wherein the protease and the cellulase are in solution in the liquid washing or cleaning agent.

* * * * *